United States Patent [19]

Russo

[11] Patent Number: 4,573,965

[45] Date of Patent: Mar. 4, 1986

[54] DEVICE FOR DRAINING WOUNDS

[75] Inventor: Ronald D. Russo, Barrington, R.I.

[73] Assignee: Superior Plastic Products Corp., Cumberland, R.I.

[21] Appl. No.: 580,091

[22] Filed: Feb. 13, 1984

[51] Int. Cl.$^4$ ............................................. A61M 27/00
[52] U.S. Cl. ..................................... 604/30; 604/31; 604/35; 604/43; 604/45; 604/128; 604/247
[58] Field of Search .................... 604/128, 30, 31, 35, 604/43, 45, 247

[56] References Cited

U.S. PATENT DOCUMENTS

| | | | |
|---|---|---|---|
| 2,930,378 | 3/1960 | Buyers | 604/45 |
| 4,084,606 | 4/1978 | Mittleman | 604/30 |
| 4,294,251 | 10/1981 | Greenwald et al. | 604/43 |

Primary Examiner—Curtis R. Davis
Attorney, Agent, or Firm—Salter & Michaelson

[57] ABSTRACT

A device for draining wounds comprises an elongated catheter member having first and second lumens, an antibacteria filter received in communication with the second lumen adjacent the proximal end thereof and a check valve which is interposed between the proximal end of said second lumen and the filter. The distal end of the catheter member is receivable in a wound for draining the wound via suction applied to the proximal end of the first lumen, and a venting effect is provided by the second lumen through the filter and the check valve. The check valve prevents the backflow of liquids through the second catheter member into the filter to prevent the clogging thereof.

5 Claims, 3 Drawing Figures

DEVICE FOR DRAINING WOUNDS

BACKGROUND AND SUMMARY OF THE INVENTION

The instant invention relates to a device for draining wounds in the human body and more particularly to a wound drain device which is operable for both sumping and irrigating wounds and which includes an elongated catheter member having two longitudinally extending lumens therethrough.

It has frequently been found to be important and beneficial to provide some means of removing substances such as blood, pus, and bile from wounds, particularly following surgery, in order to avoid and/or control infections. In this regard, a number of wound drain systems of the type which include catheter members which can be installed so that they extend directly into wounds have heretofore been available. Systems of this general type have been available for use in irrigating applications wherein irrigating fluids are introduced directly into wounds, as well as for sumping applications wherein suction is applied to wounds in order to remove unwanted substances therefrom.

While a variety of types of wound drain devices have heretofore been available, the most common types of devices have been constructed with catheter members having three elongated lumens which extend longitudinally therethrough so that the devices are operable for both sumping and irrigating wounds. A wound drain device of this type is generally installed in a patient so that the distal end of the catheter member is received in a wound, and then the catheter member is secured to the patient by suturing or the like adjacent the wound. For operation of a device of this type, a suction source is applied to the proximal end of a first of the lumens in order to apply suction to the wound. A second lumen of the catheter member is used for providing a venting effect to the wound during the application of suction via the first lumen so that the suction which is applied to the wound does not reach a level which could cause tissue damage. In order to prevent bacteria from entering the wound through the second lumen, an antibacteria filter is provided on the proximal end thereof for filtering the air which is introduced into the wound. The third lumen of the catheter member of the device is utilized for irrigating the wound. Specifically, when it becomes necessary or desirable to apply an irrigating fluid to the wound, the fluid is introduced directly into the wound via the third lumen; and then after the wound has been exposed to the fluid, it is withdrawn through the first lumen by means of the suction which is continually applied thereto. During periods when the third lumen is not used for irrigating the wound, it is blocked off or otherwise closed to prevent unfiltered air, which may contain bacteria, from entering the wound.

While devices of the above-described type have frequently been used for draining and irrigating wounds, they have not always been entirely effective for several reasons. First, when a wound drain device is used for providing a sumping effect, there can be a tendency for fluids to back up into the second lumen so that the fluids eventually clog the antibacteria filter connected thereto. When this occurs, the second lumen loses its effectiveness for providing a venting effect, and as a result, suction levels can be reached at the distal end of the first lumen which are far in excess of the suction levels which can be tolerated in a wound without causing tissue damage. For this reason, it has been necessary for nurses and other medical personnel to carefully monitor devices of this type to be sure that the second lumens of the catheter members thereof are maintained free and unobstructed so that suction levels which could cause tissue damage are avoided. Another disadvantage of the heretofore known wound drain systems of the hereinabove described type is the fact that they have required catheter members having three lumens therethrough. In order to provide a catheter member which has three lumens therethrough, it is necessary for the sectional dimension of the catheter member to be relatively large, and therefore a relatively large opening in a wound is necessary in order to accommodate such a catheter member. This obviously adds to patient discomfort and can even have the effect of impeding the overall healing process.

The instant invention provides a novel device which overcomes the disadvantages of the heretofore known wound drain systems. The device of the instant invention comprises a catheter member having only two lumens therethrough, an antibacteria filter, and a check valve element. A first lumen of the catheter member is used for applying suction to a wound. The check valve element and the antibacteria filter are positioned in in-line communication with a second lumen of the catheter member so that the filter is operative for filtering air which is drawn into the second lumen from the atmosphere and so that the check valve element prevents the backflow of fluids through the second lumen into the filter. In the preferred embodiment of the device, a check valve housing is provided attached to the proximal end of the second lumen of the catheter member, and the check valve element is disposed within the check valve housing. The filter is mounted in the housing so that the check valve element is interposed between the filter and the proximal end of the second lumen of the catheter member. The check valve element preferably comprises a duckbill-type check valve element, and in one embodiment of the device an irrigation port which is selectively closable is provided in the check valve housing. The irrigation port is positioned in the housing so that it communicates with the second lumen for supplying irrigating fluids to a wound therethrough and so that the check valve element prevents communication between the irrigation port and the filter in a direction towards the filter, whereby the backflow of fluids from the irrigation port into the filter is avoided. Accordingly, in this embodiment of the device, the second lumen can alternately be used for providing a sumping effect or for conducting irrigating fluids to a wound.

As a result of the above, the instant invention provides an effective device which can alternately be used for providing a sumping effect for draining a wound or for providing a means for irrigating a wound. However, since the device of the instant invention requires only two lumens in the catheter member thereof in order to provide these two functions, the catheter member can be constructed with a reduced sectional dimension in order to minimize patient discomfort and also to minimize the possibility of the catheter member impeding the healing process. The instant invention also provides an effective device for wound sumping applications wherein the risk of exposing tissue in the wound to excessive suction levels is effectively minimized.

Accordingly, it is a primary object of the instant invention to provide a device for draining wounds and the like which includes an antibacterial filter and a check valve element for preventing the backflow of fluids into the filter.

Another object of the instant invention is to provide a wound drain device which includes a catheter member having first and second lumens therethrough and an antibacteria filter for filtering air which enters one of the lumens, wherein a check valve is provided for preventing the backflow of fluids into the filter to prevent the clogging thereof.

Another object of the instant invention is to provide a device for draining wounds which can alternately be used for sumping or irrigating wounds.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention.

DESCRIPTION OF THE INVENTION

Figure 1:
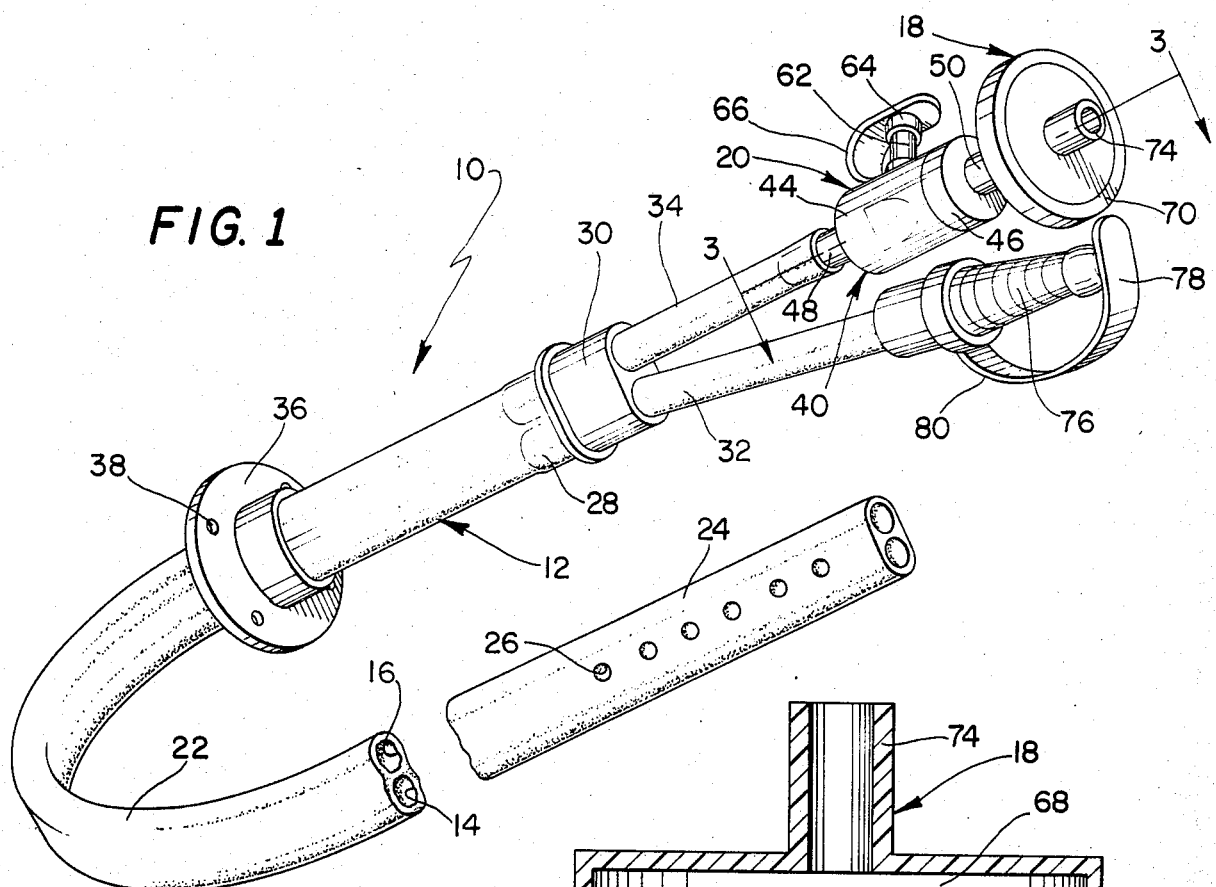
FIG. 1 is a fragmentary perspective view of the device of the instant invention.
Figure 2:
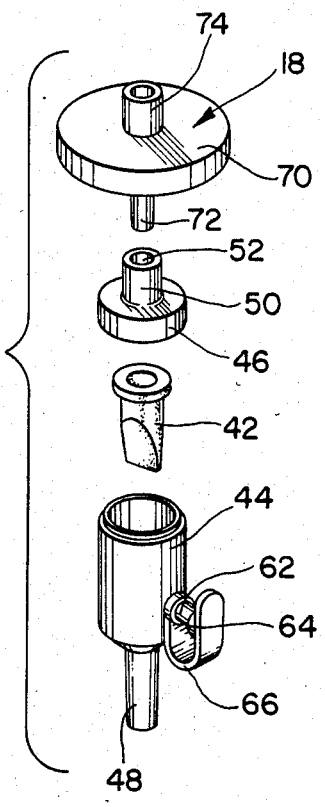
FIG. 2 is an exploded perspective view of the filter and the check valve assembly of the device.
Figure 3:
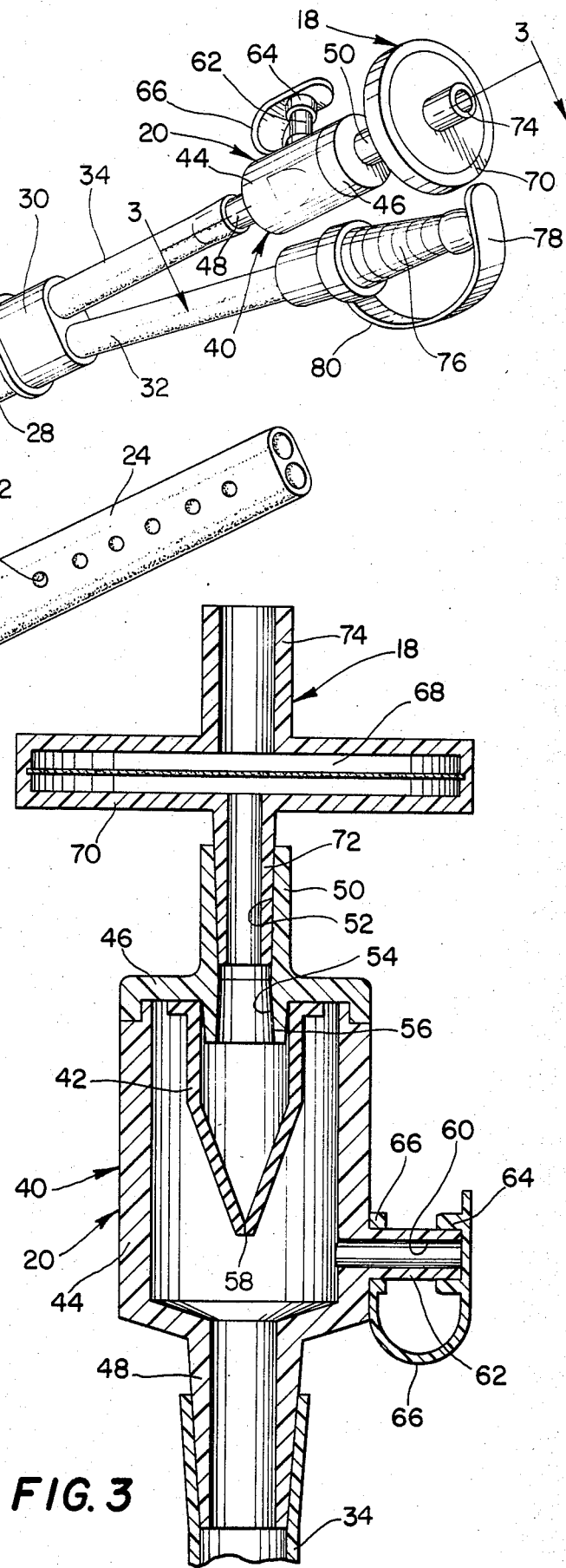
FIG. 3 is a sectional view taken along line 3—3 in FIG. 1.

Referring now to the drawing, the device for draining wounds of the instant invention is illustrated and generally indicated at 10 in FIG. 1. The device 10 comprises an elongated catheter member generally indicated at 12 having first and second lumens 14 and 16, respectively, therethrough, an antibacteria filter generally indicated at 18, and a check valve assembly generally indicated at 20. The filter 18 and the check valve assembly 20 are mounted in the device 10 so that they are in in-line communication with the second lumen 16. Specifically, the filter element 18 and the check valve assembly 20 are mounted on the second lumen 16 so that the filter element 18 is operative for filtering air which enters into the second lumen 16 and so that the check valve assembly 20 is operative for preventing the backflow of fluids from the second lumen 16 into the filter element 18.

The catheter member 12 comprises an elongated tubular member 22 through which the first and second lumens 14 and 16 extend, the tubular member 22 preferably being constructed of a soft, flexible, nontoxic silicone rubber material which can be received and maintained in a wound of a patient for an extended period of time with a minimum of discomfort. A first or distal end 24 of the tubular member 22 is formed with a plurality of suction apertures 26 therethrough which provide communication between the first and second lumens 14 and 16, respectively, and also between each of the lumens 14 and 16 and the exterior of the tubular member 22. A second or proximal end 28 of the tubular member 22 has a double plug adaptor 30 received therein, and first and second tubular extensions 32 and 34, respectively, extend from the plug adaptor 30 and communicate with the first and second lumens 14 and 16, respectively. Further included in the catheter member 12 is a flanged collar 36 which is received on the tubular member 22 and which is preferably also constructed of a relatively soft, flexible, nontoxic silicone rubber material. The collar 36 has a plurality of apertures 38 formed in the flange portion thereof, and it is preferably dimensioned and configured so that it is snugly received on the tubular member 22 and slidable thereon, but so that once it is positioned in a desired location along the extent of the member 22, a natural grasping effect is achieved between the rubberized collar 36 and the rubberized tubular member 22 to retain the collar 36 in the desired location until it is manually repositioned.

The check valve assembly 20 is received in the second tubular extension 34 so that it communicates with the second lumen 16. The check valve assembly 20 preferably comprises a housing generally indicated at 40 and a check valve element 42. The housing 40 is preferably constructed of a substantially rigid transparent plastic material, and it includes a lower housing portion 44 and an upper cap portion 46 which is received and secured on the lower portion 44. Extending from the lower end of the lower portion 44 is a tapered end 48 which is received in the second tubular extension 34, and a tubular end 50 extends from the cap portion 46 and defines a tapered socket 52. The socket 52 communicates with the interior of the housing 40 through an opening 54, and an inner boss 56 extends around the opening 54 in the housing 40. The check valve element 42 preferably comprises a duckbill-type check valve element, and it is constructed of a flexible rubberized material in a tapered configuration, having a terminal slot 58. The check valve element 42 is preferably sealingly received on the boss 56 so that leakage between the boss 56 and the check valve element 42 is avoided and so that the slot 58 provides the only communication between the opening 54 and the interior of the housing 40. In the embodiment of the instant invention herein illustrated, an irrigation port 60 is integrally formed in the lower housing portion 44. The irrigation port 60 is defined by a tubular element 62, and a closure cap 64 having a flexible retainer member 66 integrally formed therewith which is received on the tubular element 62. The closure cap 64 provides a closure member which is preferably receivable on the tubular element 62 in airtight relation to provide an airtight seal for the port 60, and the retainer member 66 retains the cap 64 adjacent the tubular element 62 when it is removed from the port 60. It will be understood, however, that other embodiments of the instant invention which are not adapted for irrigation applications and which therefore have check valve assemblies which are constructed without irrigation ports are also contemplated.

The filter 18 preferably comprises a conventional antibacteria filter of the type used in conventional wound drain systems for sumping applications. In this regard, the filter 18 preferably comprises a filter element 68 and a filter housing 70 in which the element 68 is contained, the housing 70 preferably being made of a substantially rigid, transparent plastic material. Integrally formed with the housing 70 is a tapered end 72 which is received in the socket 52, and a tubular end 74 is provided on the opposite extremity of the filter 18 from the end 72. The filter element 68 comprises a conventional filter element of the type which is operative for filtering bacteria from an airstream passing therethrough; and, accordingly, when it is mounted in the manner herein illustrated, air passing through the tubular end 74 is filtered by the filter element 68 before it passes through the tapered end 72 and into the check valve assembly 20.

The wound drain device 10 further comprises a tapered plug 76 for interconnecting the first lumen 14 to an appropriate source of suction or vacuum. The tapered plug 76 is received on the first extension 32, and a closure member 78 is receivable on the end of the plug 76 and includes a retainer element 80 for retaining it adjacent the plug 76 when it is removed from the end thereof.

For use and operation of the device 10, the distal end 24 is positioned in a wound in a patient, and the catheter member 12 is retained in a desired location relative to the patient by means of the collar 36. Specifically, the collar 36 is sutured to the patient using the apertures 38; or it is taped to the skin of the patient to maintain it adjacent the point where the tubular member 22 extends from the wound. During use of the device 10 for sumping applications, a vacuum source is applied to the first lumen 14 via the tapered plug 76 in order to remove unwanted substances, such as blood, pus, bile, etc., from the wound. In order to provide an even level of suction which is within the range which is tolerable by the patient without causing tissue damage in the wound, a venting effect is provided by the second lumen 16, air being drawn into the wound through the second lumen 16 by the vacuum transmitted to the wound via the first lumen 14. The air passing into the second lumen 16 is filtered by the filter 18 so that it is substantially free from bacteria in order to avoid introducing infectious bacteria into the wound which could be present in unfiltered air. After the air passes through the filter 18, it enters the check valve 20, passing through the check valve element 42 thereof, and finally it passes into the second lumen 16. In the event of a backup of fluid from the wound into the second lumen 16, the check valve element 42 prevents this fluid from reaching the filter 18. Accordingly, the filter element 68 remains free and clear so that air can pass therethrough and into the second lumen 16 to relieve the suction in the wound as needed. In the event that it becomes necessary or desirable to operate the device 10 for irrigating the wound, the cap 64 is removed from the tubular element 62, and an irrigating fluid is introduced into the port 60 so that it travels to the wound via the second lumen 16. The fluid is thereafter withdrawn from the wound via the lumen 14 as a result of the suction which is applied thereto.

It is seen, therefore, that the instant invention provides an effective wound drain device which can be alternately used for sumping or irrigating applications. In contrast to the heretofore known devices which have been operative for both sumping and irrigating, the device of the instant invention requires only two lumens, and therefore the catheter member of the device of the instant invention can be constructed with a reduced sectional dimension. Further, when the device is used for sumping applications, the check valve element 42 effectively prevents the backflow of fluids into the filter 18 so that the filter 18 remains free and clear and does not require frequent monitoring or changing. Because the check valve element 42 reliably prevents fluids from the wound from reaching the filter 18 so that it does not tend to become plugged, the risks of exposing an area of a wound to excessive vacuum levels are substantially reduced. Accordingly, it is seen that the device of the invention represents a significant advancement in the medical art which has substantial merit from the standpoint of maximizing patient safety as well as from a commercial standpoint.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A device for draining wounds and the like comprising:
    (a) a catheter member having distal and proximal ends and having first and second longitudinally extending lumens therethrough;
    (b) an antibacteria filter mounted in in-line communication with said second lumen for filtering gases passing therethrough; and
    (c) a check valve element mounted in in-line communication with said second lumen and with said filter so that gases can flow through said filter and through said second lumen toward said second lumen distal end but so that fluids from a wound adjacent said second lumen distal end are prevented from flowing back through said second lumen and into said filter, whereby blockage of said filter as a result of backflow of said fluids is prevented.

2. In the device of claim 1, said check valve element and said filter being mounted adjacent the proximal end of said catheter member.

3. In the device of claim 1, said check valve comprising a check valve housing mounted on the proximal end of said catheter member in in-line communication with said second lumen, and a check valve element mounted in said housing so that said check valve element is in in-line communication with said second lumen, said filter being mounted on said housing so that said check valve element is interposed between said filter and said catheter member second lumen.

4. In the device of claim 3, said check valve element further characterized as a duckbill-type check valve element.

5. In the device of claim 3, said check valve housing having an irrigation port therein which communicates through said housing with said first lumen, said check valve element preventing communication between said irrigation port and said filter in a direction toward said filter, said device further comprising means for selectively closing said irrigation port.

* * * * *